US011808726B2

(12) United States Patent
Hayashi (10) Patent No.: US 11,808,726 B2
(45) Date of Patent: Nov. 7, 2023

(54) SENSOR AND METHOD FOR MANUFACTURING THE SAME

(71) Applicant: KABUSHIKI KAISHA TOSHIBA, Tokyo (JP)

(72) Inventor: Yumi Hayashi, Ayase Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 108 days.

(21) Appl. No.: 17/173,161

(22) Filed: Feb. 10, 2021

(65) Prior Publication Data
US 2022/0011254 A1    Jan. 13, 2022

(30) Foreign Application Priority Data
Jul. 8, 2020    (JP) .............................. JP2020-117689

(51) Int. Cl.
*G01N 33/00*    (2006.01)
*G01N 27/22*    (2006.01)

(52) U.S. Cl.
CPC ......... *G01N 27/227* (2013.01); *G01N 33/005* (2013.01)

(58) Field of Classification Search
CPC .... G01N 27/227; G01N 33/005; G01N 33/00; G01N 27/22; G01N 2027/22; G01N 27/286; G01N 27/3275; G01N 27/02; G01N 33/0036; G01N 33/0031; G01N 33/0004; G01N 33/0009; G01N 1/22
See application file for complete search history.

(56) References Cited

U.S. PATENT DOCUMENTS

| 2013/0186178 | A1 |   | 7/2013 | Usagawa |
| 2019/0086377 | A1 |   | 3/2019 | Ikehashi et al. |
| 2019/0162694 | A1 | * | 5/2019 | Hayashi ............ G01N 27/4074 |
| 2020/0300803 | A1 |   | 9/2020 | Hayashi et al. |

FOREIGN PATENT DOCUMENTS

| DE | 112016004203 T5 | * | 6/2018 | ............. G01N 25/22 |
| JP | 2004-144627 A |   | 5/2004 | |
| JP | 2012-73154 A |   | 4/2012 | |
| JP | 2019-56607 A |   | 4/2019 | |
| JP | 2019-100705 A |   | 6/2019 | |
| JP | 2020-153709 A |   | 9/2020 | |
| WO | WO-2019188904 A1 | * | 10/2019 | ........... G01N 27/225 |

* cited by examiner

*Primary Examiner* — Natalie Huls
*Assistant Examiner* — James I Burris
(74) *Attorney, Agent, or Firm* — Finnegan, Henderson, Farabow, Garrett & Dunner, LLP (57) ABSTRACT

According to one embodiment, a sensor includes a sensor part including a first film. The first film includes a first element including at least one selected from the group consisting of Pd, Pt, and Au. The first film includes a first region, and a second region including a plurality of protrusions. A protruding direction of the protrusions is along a first direction from the first region toward the second region.

13 Claims, 5 Drawing Sheets

SENSOR AND METHOD FOR MANUFACTURING THE SAME

CROSS-REFERENCE TO RELATED APPLICATIONS

This application is based upon and claims the benefit of priority from Japanese Patent Application No. 2020-117689, filed on Jul. 8, 2020; the entire contents of which are incorporated herein by reference.

FIELD

Embodiments of the invention generally relate to a sensor and a method for manufacturing a sensor.

BACKGROUND

For example, it is desirable to improve the detection performance of a sensor.

DETAILED DESCRIPTION

According to one embodiment, a sensor includes a sensor part including a first film. The first film includes a first element including at least one selected from the group consisting of Pd, Pt, and Au. The first film includes a first region, and a second region including a plurality of protrusions. A protruding direction of the protrusions is along a first direction from the first region toward the second region.

According to one embodiment, a sensor includes a sensor part including a first film. The first film includes a first element including at least one selected from the group consisting of Pd, Pt, and Au. The first film includes a first surface, a second surface, a first region, and a second region. The first region is located between the first surface and the second surface. The second region is located between the first region and the second surface. The second surface is rougher than the first surface.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1A:
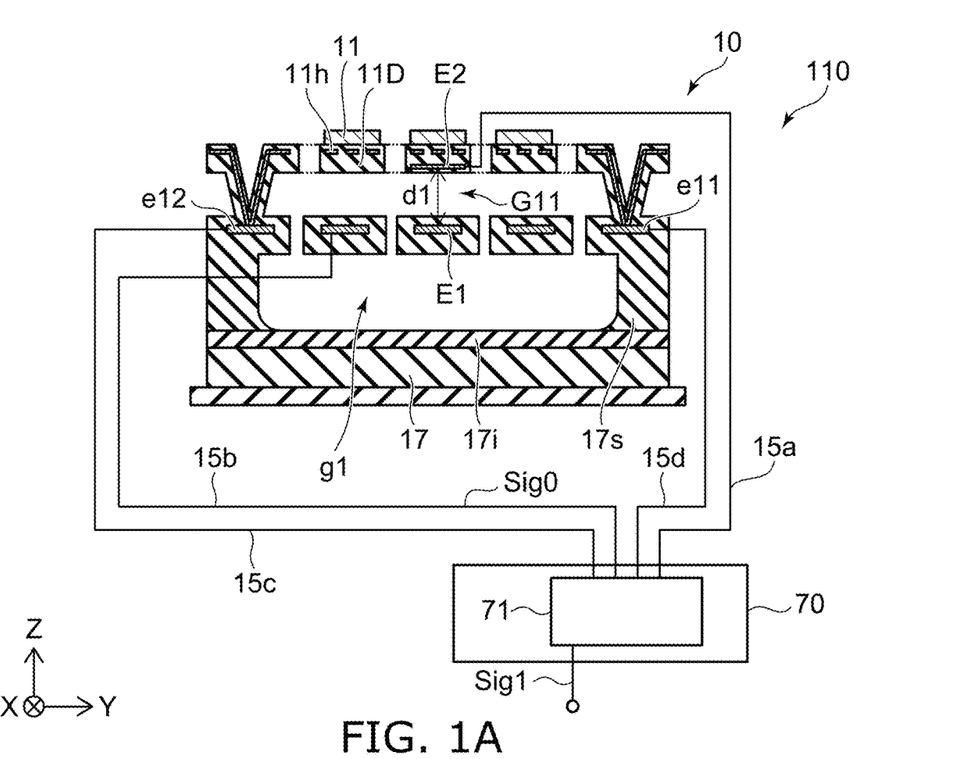
FIGS. 1A and 1B are schematic cross-sectional views illustrating a sensor according to a first embodiment.
Figure 1B:
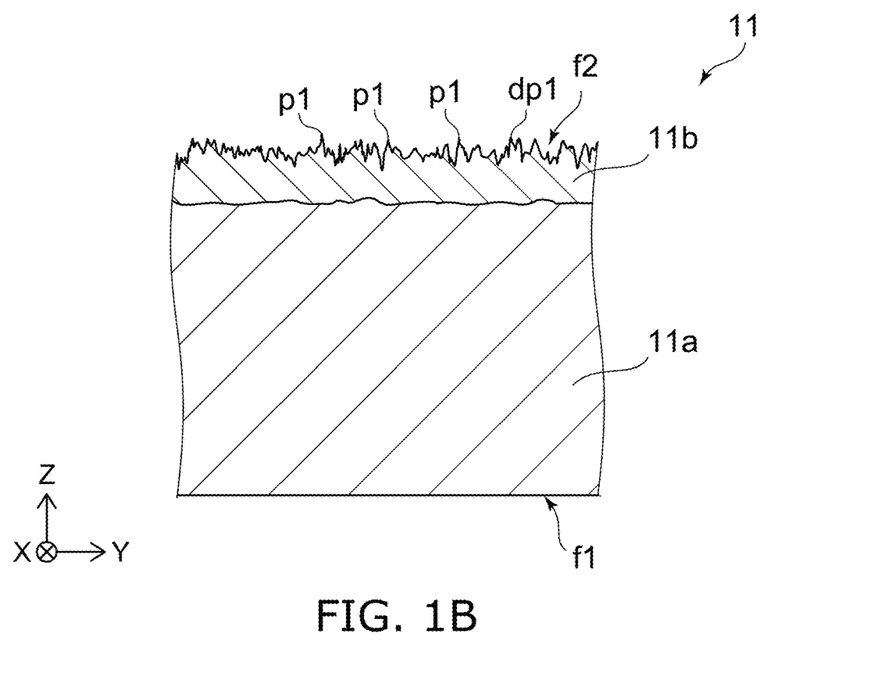

FIGS. 1A and 1B are schematic cross-sectional views illustrating a sensor according to a first embodiment.

As shown in FIG. 1A, the sensor 110 according to the embodiment includes a sensor part 10. The sensor part 10 includes a first film 11. FIG. 1B is an enlarged view of the first film 11 shown in FIG. 1A.

The first film 11 includes a first element. The first element includes at least one selected from the group consisting of Pd, Pt, and Au. The first film 11 may include at least one of a second element or a third element, which are described below. For example, the sensor 110 is a gas sensor that is configured to detect a gas including a fourth element (e.g., hydrogen).

A controller 70 may be provided as shown in FIG. 1A. The controller 70 includes, for example, a detection circuit 71. The detection circuit 71 is configured to output a detection signal Sig1. The detection signal Sig1 changes according to the concentration of the fourth element included in a gas around the sensor part 10. An example of the detection operation of the sensor part 10 is described below.

As shown in FIG. 1B, the first film 11 includes a first region 11a, and a second region 11b that includes multiple protrusions p1. The second region 11b is located on the first region 11a. For example, the second region 11b is continuous with the first region 11a. The multiple protrusions p1 are provided in the front surface of the second region 11b (the front surface of the first film 11). For example, a "turf-like nanostructure" is formed of the multiple protrusions p1.

The direction from the first region 11a toward the second region 11b is taken as a Z-axis direction (a first direction). One direction perpendicular to the Z-axis direction is taken as an X-axis direction. A direction perpendicular to the Z-axis direction and the X-axis direction is taken as a Y-axis direction. The first film 11 spreads along the X-Y plane.

The protruding direction of the multiple protrusions p1 is along the first direction. The protruding direction of the multiple protrusions p1 includes a first-direction component.

The first film 11 includes a first surface f1 and a second surface f2. The first surface f1 is, for example, the lower surface of the first film 11 (the lower surface of the first region 11a). The second surface f2 is, for example, the upper surface of the first film 11 (the upper surface of the second region 11b). The first region 11a is between the first surface f1 and the second surface f2. The second region 11b is between the first region 11a and the second surface f2.

The second surface f2 includes an unevenness dp1. The multiple protrusions p1 correspond to protruding portions; and the peripheries of the protrusions p1 correspond to recesses (holes). The second surface f2 is rougher than the first surface f1. The surface area of the second surface f2 is greater than the surface area of the first surface f1.

For example, the first film 11 can store the fourth element (e.g., hydrogen, etc.). For example, the fourth element (e.g., hydrogen, etc.) adsorbs to the first film 11. When the first film 11 stores the fourth element, the characteristics of the first film 11 change. For example, when the first film 11 stores the fourth element, the first film 11 expands, and the volume of the first film 11 increases. A characteristic (e.g., the volume, etc.) of the first film can change according to the change of the concentration of the fourth element included in the gas at the periphery of the first film 11. For example, the shape of the first film 11 changes according to the concentration of the fourth element included in the gas around the sensor part 10. The existence or absence of the fourth element or the concentration of the fourth element at the periphery of the first film 11 can be detected by detecting a signal corresponding to the change of the characteristics of the first film 11.

Due to the multiple protrusions p1, the surface area of the second region 11b (the second surface f2) is greater than the surface area of the first surface f1. Therefore, for example, the first film 11 can effectively incorporate a trace amount of the fourth element included in the gas around the sensor part 10. Thereby, the sensor 110 can detect the fourth element (hydrogen, etc.) with high sensitivity. According to the embodiment, the detection performance of the sensor can be improved.

The second region 11b is, for example, a catalyst layer. In one example, the second region 11b dissociates hydrogen molecules into hydrogen atoms. By the catalyst effect of the catalyst layer, the hydrogen can be efficiently incorporated into the first film 11. The first region 11a is, for example, a film stress-change layer. The volume of the film stress-change layer expands or contracts due to the absorption or the desorption of the fourth element. For example, the film stress of the first region 11a changes when the first region 11a incorporates hydrogen atoms.

In the example as shown in FIG. 1A, the sensor part 10 includes a first electrode E1 and a second electrode E2. The first electrode E1 is separated from the first film 11. A gap G11 is provided between the first film 11 and the first electrode E1. For example, the second electrode E2 is fixed to the first film 11. An electrical signal that is generated between the first electrode E1 and the second electrode E2 changes according to the change of the characteristics (e.g., the volume) of the first film 11. By detecting the change of the electrical signal, the existence or absence of the fourth element or the concentration of the fourth element at the periphery of the first film 11 can be detected.

For example, a film portion 11D (e.g., a diaphragm) in which the first film 11 is provided deforms when the first film 11 expands. The deformation of the film portion 11D is caused by stress generated by the expansion of the first film 11. A distance d1 between the first electrode E1 and the second electrode E2 changes when the film portion 11D deforms. The electrostatic capacitance between the first electrode E1 and the second electrode E2 changes when the distance d1 between the first electrode E1 and the second electrode E2 changes. By detecting the change of the electrostatic capacitance, the existence or absence of the fourth element or the concentration of the fourth element at the periphery of the first film 11 can be detected. In the example, the sensor part 10 has a MEMS (Micro Electro Mechanical Systems) structure.

As described above, for example, the controller 70 includes the detection circuit 71. The detection circuit 71 is electrically connected to the first and second electrodes E1 and E2. For example, the detection circuit 71 is electrically connected to the second electrode E2 by wiring 15a. For example, the detection circuit 71 is electrically connected to the first electrode E1 by wiring 15b. The detection circuit 71 is configured to output the detection signal Sig1. The detection signal Sig1 changes according to the concentration of the fourth element (e.g., hydrogen) included in the gas around the sensor part 10.

Thus, in one example, the distance d1 between the first electrode E1 and the second electrode E2 (the distance of the gap G11) changes according to the concentration of the fourth element included in the gas around the sensor part 10. The fourth element can be detected by detecting the change of the distance d1 as the change of the electrostatic capacitance. According to the embodiment, other characteristics (e.g., the conductivity, etc.) of the first film 11 may change according to the concentration of the fourth element included in the gas at the periphery of the sensor part 10. The fourth element can be detected by detecting the change of the other characteristic.

For example, a sensor signal Sig0 can be output from the sensor part 10. The sensor signal Sig0 is generated between the first electrode E1 and the second electrode E2. For example, the sensor signal Sig0 is generated between the wiring 15a and the wiring 15b. The sensor signal Sig0 changes according to the concentration of the fourth element included in the gas around the sensor part 10. For example, the detection signal Sig1 that is output from the detection circuit 71 corresponds to the sensor signal Sig0. The detection circuit 71 can process the sensor signal Sig0 and output the processed sensor signal Sig0 as the detection signal Sig1. The processing may include, for example, amplification. The amplification may include deriving a difference between a reference value. The controller 70 may include, for example, a CPU (Central Processing Unit), etc. At least a portion of the controller 70 may be included in the sensor 110. At least a portion of the controller 70 may be provided separately from the sensor 110.

In the example, the film portion 11D of the sensor part 10 includes a heater 11h. For example, the first element that is stored in the first film 11 can be desorbed from the first film 11 by the heater 11h increasing the temperature of the first film 11. For example, a portion of the heater 11h is electrically connected to an electrode e12. The electrode e12 is electrically connected to the detection circuit 71 by wiring 15c. For example, another portion of the heater 11h is electrically connected to an electrode e11. The electrode e11 is electrically connected to the detection circuit 71 by wiring 15d.

In the example, the sensor part 10 includes a substrate 17, an insulating film 17i, and a supporter 17s. The insulating film 17i is located on the substrate 17; and the supporter 17s is located on the insulating film 17i. The first electrode E1 is supported by the supporter 17s. For example, a gap g1 may be provided between the first electrode E1 and the substrate 17 (and the insulating film 17i). Insulating portions may be provided at the upper and lower surfaces of the first electrode E1.

The supporter 17s supports the film portion 11D. Thereby, the gap G11 can be formed between the film portion 11D and the portion including the first electrode E1. The distance d1 between the first electrode E1 and the second electrode E2 included in the film portion 11D can be changed thereby.

For example, the direction from the first electrode E1 toward the second electrode E2 is along the Z-axis direction. For example, the distance d1 between the first electrode E1 and the second electrode E2 is the length along the Z-axis direction. The film portion 11D is along the X-Y plane. For example, the second electrode E2 that is included in the film portion 11D is displaced in the Z-axis direction due to the change of the characteristics of the first film 11 according to the concentration of the fourth element around the sensor part 10.

According to the embodiment as described above, the first film 11 can effectively incorporate the fourth element by increasing the surface area of the second region 11b (the second surface f2) including the multiple protrusions p1. High sensitivity is obtained thereby. The detection performance of the sensor can be improved.

In the example, the insulating film 17i is located between the substrate 17 and the first film 11 in the Z-axis direction. The first electrode E1 is located between the insulating film 17i and the first film 11 in the Z-axis direction. The second electrode E2 is located between the first electrode E1 and the first film 11 in the Z-axis direction. The heater 11h is located between the second electrode E2 and the first film 11 in the Z-axis direction.

For example, the first film 11 is exposed. The first film 11 can efficiently contact the gas including the fourth element. The temperature of the first film 11 can be efficiently increased by the heater 11h. Thereby, the fourth element that is stored in the first film 11 can be efficiently desorbed from the first film 11.

When the fourth element is hydrogen, the first element (at least one selected from the group consisting of Pd, Pt, and Au) that is included in the first film 11 may function as a catalyst. The first region 11a and the second region 11b each may include the first element. The concentration (at %) of the first element in the second region 11b may be about equal to (not less than 0.9 times and not more than 1.1 times) the concentration (at %) of the first element in the first region 11a.

When the fourth element is hydrogen, for example, a high reaction rate is obtained by the first film 11 including the second element (at least one selected from the group consisting of Si, P, and B). For example, bonds with hydrogen do not occur easily. The concentration (at %) of the second element in the second region 11b is less than the concentration (at %) of the second element in the first region 11a. Or, the second region 11b may not include the second element.

When the fourth element is hydrogen, for example, a high reaction rate is obtained by the first film 11 including the third element (at least one selected from the group consisting of Cu, Ag, Ni, Au, Fe, and Cr). The first region 11a and the second region 11b each may include the third element. The concentration (at %) of the third element in the second region 11b may be about equal to (not less than 0.9 times and not more than 1.1 times) the concentration (at %) of the third element in the first region 11a.

For example, the second region 11b includes oxygen. For example, the first region 11a does not include oxygen, or the oxygen concentration (at %) in the first region 11a is less than the oxygen concentration (at %) in the second region 11b.

Figure 2A:
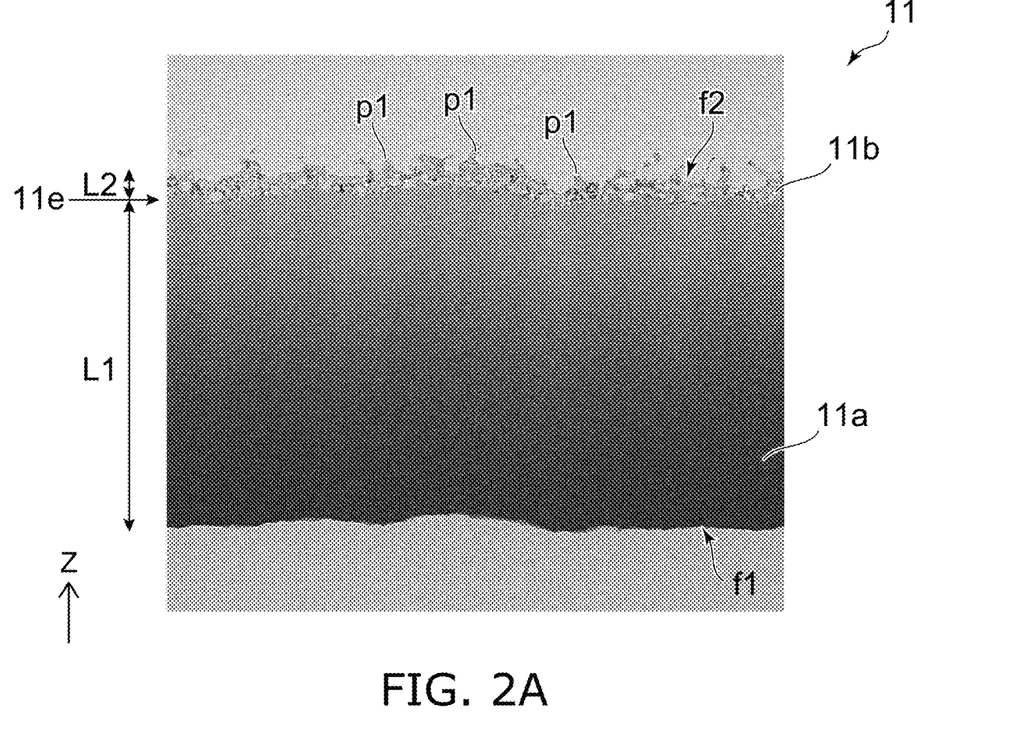
FIGS. 2A and 2B are cross-section observation images illustrating a portion of the sensor according to the first embodiment.
Figure 2B:
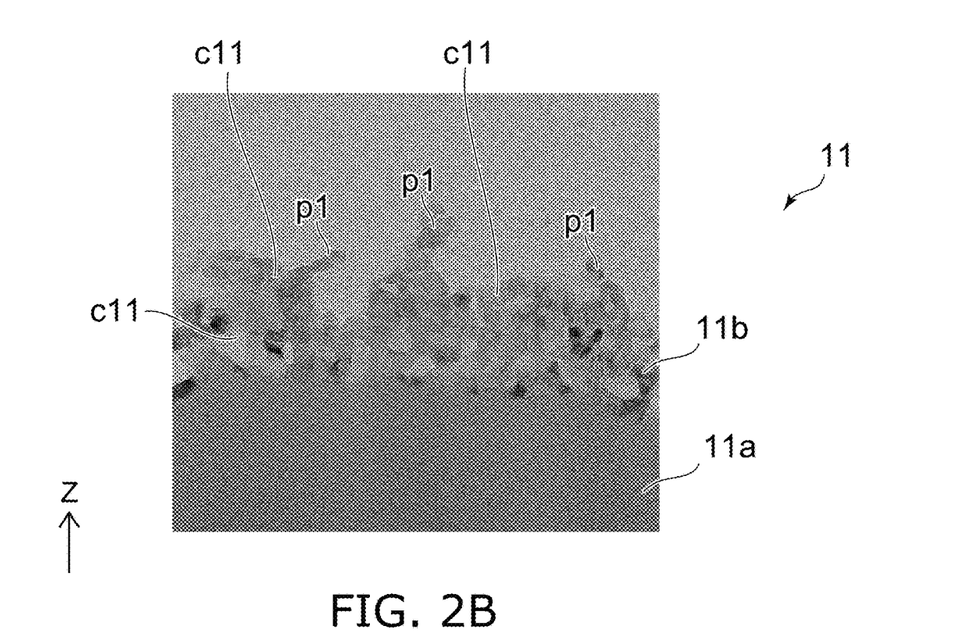

FIGS. 2A and 2B are cross-section observation images illustrating a portion of the sensor according to the first embodiment.

These images are obtained by TEM (Transmission Electron Microscope). FIG. 2A corresponds to FIG. 1B. FIG. 2B is an enlarged image of a portion of FIG. 2A.

As shown in FIG. 2A, a thickness L2 of the second region 11b is, for example, not less than 0.1 nm and not more than 1000 nm. The thickness L2 is the average value of the length of the second region 11b along the Z-axis direction (the distance to the second surface f2 from a boundary 11e between the first region 11a and the second region 11b). A thickness L1 of the first region 11a is, for example, not less than 1 nm and not more than 10 μm. The thickness L1 is the average value of the length of the first region 11a along the Z-axis direction (the distance from the first surface f1 to the boundary 11e).

According to the embodiment as shown in FIG. 2B, for example, the first region 11a is amorphous; and the second region 11b includes a crystal grain c11. Or, the crystallinity of the second region 11b is greater than the crystallinity of the first region 11a. For example, the crystal grain c11 of the second region 11b is larger than the crystal grain of the first region 11a. For example, the first film 11 can efficiently store the fourth element because the first region 11a is amorphous, or the crystallinity of the first region 11a is low.

For example, the average grain size of the crystal grain c11 of the second region 11b is not less than 0.1 nm and not more than 100 nm. For example, the average value of the equivalent circular diameter of the crystal grain c11 at a cross section such as that of FIG. 2B, the average crystal grain size from EBSD (Electron Back Scattered Diffraction), or the like can be measured.

For example, the height of the protrusion p1 (the length in the first direction of the protrusion p1) is not less than 0.1 nm and not more than 1000 nm. For example, the height of the protrusion p1 can be measured by cross-section observation such as that of FIG. 2B, AFM (Atomic Force Microscopy), etc.

For example, the width of the protrusion p1 (the length of the protrusion p1 in a second direction that is perpendicular to the first direction) is not less than 0.1 nm and not more than 1000 nm. For example, the width of the protrusion p1 can be verified by cross-section observation such as that of FIG. 2B, AFM (Atomic Force Microscopy), etc. Due to such a shape, the surface area of the second region 11b can be wide, and the incorporation efficiency of the fourth element can be increased.

Figure 3A:
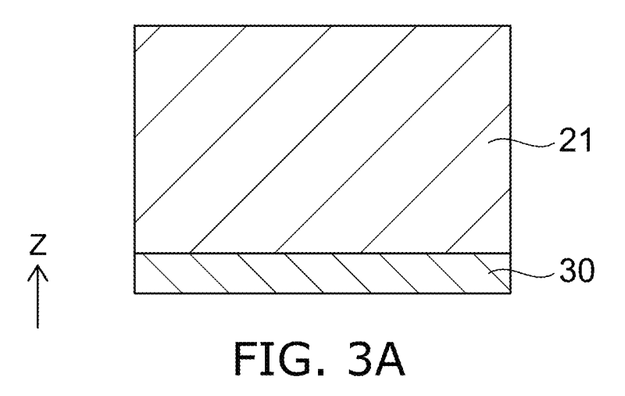
FIGS. 3A to 3C are schematic cross-sectional views illustrating a method for manufacturing the sensor according to the first embodiment.
Figure 3B:
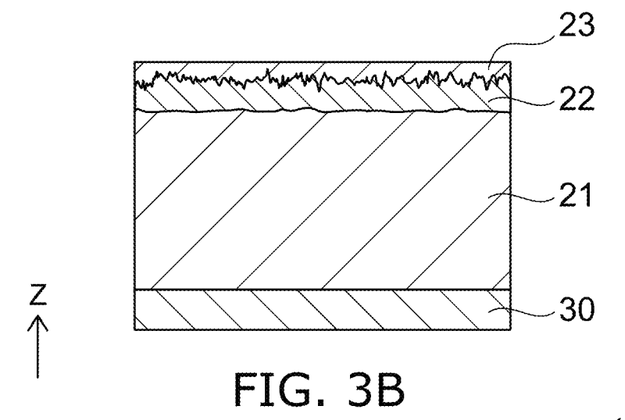
Figure 3C:
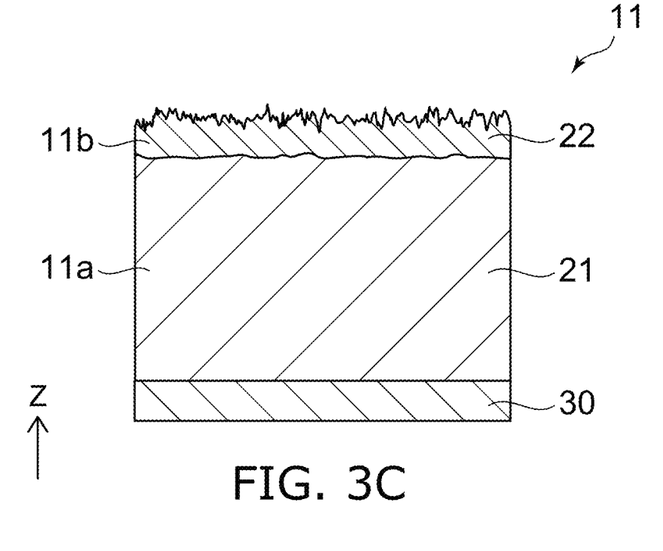

FIGS. 3A to 3C are schematic cross-sectional views illustrating a method for manufacturing the sensor according to the first embodiment.

FIGS. 3A to 3C show an example of the method for manufacturing the first film 11. A first layer 21 is prepared as shown in FIG. 3A. The first layer 21 includes the first and second elements. For example, the first layer 21 is provided on a substrate 30 by forming a PdCuSi alloy layer by sputtering, etc.

The first film 11 described with reference to FIG. 1A (a film that includes the first region 11a, and the second region 11b located on the first region 11a) can be formed by ashing the first layer 21. The second region 11b that includes the multiple protrusions can be formed on the first region 11a by the ashing conditions. In the example, the ashing includes first processing that uses a first gas, and second processing that uses a second gas.

FIG. 3B shows the first processing. The oxygen concentration of the first gas used in the first processing is greater than the oxygen concentration of the second gas. The first gas is, for example, $O_2$ gas. For example, the PdCuSi (the first layer 21) is ashed using $O_2$ gas. Thereby, Si and the oxygen in the first gas (or the oxygen in ambient air) bond at the front surface vicinity of the PdCuSi; and a third layer 23 is formed. At this time, a second layer 22 is formed between the first layer 21 and the third layer 23. The first layer 21 corresponds to the first region 11a; and the second layer 22 corresponds to the second region 11b. For example, the second layer 22 does not include Si; or the Si concentration in the second layer 22 is less than the Si concentration in the first layer 21.

Subsequently, the second processing is performed. FIG. 3C shows the second processing. The second gas that is used in the second processing includes, for example, fluorine. The second gas includes, for example, $O_2$ and $CF_4$. By the ashing that uses such a second gas, the third layer 23 is removed; and the first film 11 that includes the first and second regions 11a and 11b is formed. The first processing may be omitted.

FIGS. 4A to 4H are graphs illustrating the sensor.

FIGS. 4A to 4H show the distribution of the number of atoms in the depth direction (the Z-axis direction). FIGS. 4A to 4D correspond to the first layer 21 shown in FIG. 3A. FIGS. 4E to 4H correspond to the first film 11 shown in FIG. 3C. The first processing is omitted for the sample. The distribution of a number of atoms Na1 along a depth Dp1 can be analyzed by performing XPS (X-ray photoelectron spectroscopy) analysis while removing the film from the front surface of the film (the layer) by Ar$^+$ ion sputtering. The position at which the depth Dp1=0 corresponds to the front surface of the film (the layer).

Figures 4A, 4B:
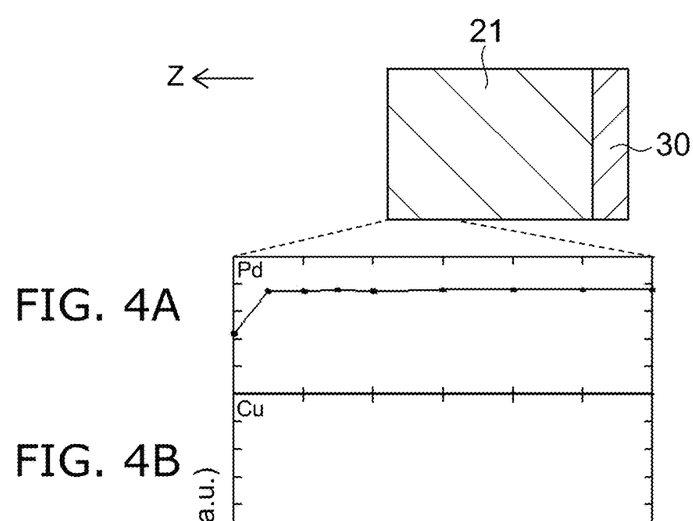
FIGS. 4A to 4H are graphs illustrating the sensor.
Figure 4C:
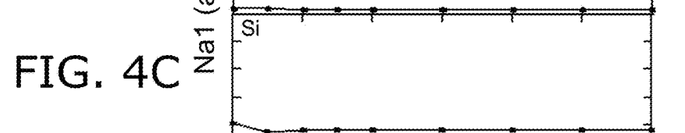
Figure 4D:
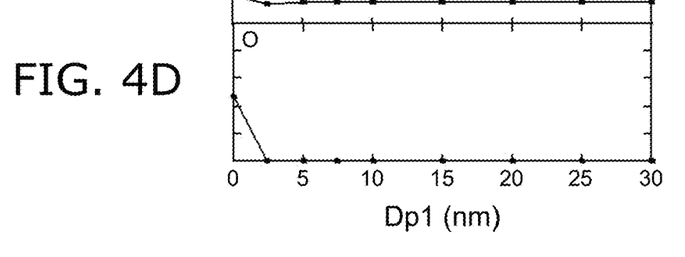
Figures 4E, 4F:
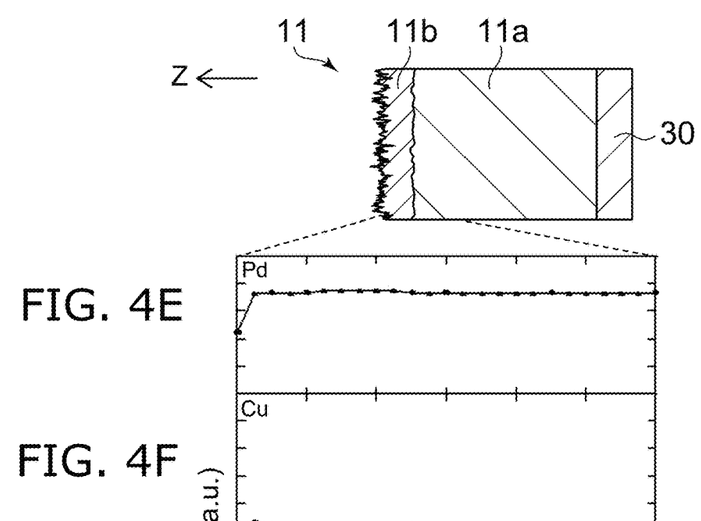

FIGS. 4A and 4E show the number of Pd atoms. The concentration of the first element (in the example, Pd) at the front surface of the first film 11 is greater than the concentration of the first element at the inner portion of the first film 11. For example, at the front surface side of the first film, the concentration of the first element is high by the amount that the Si concentration is low.

FIGS. 4B and 4F show the number of Cu atoms. The first layer 21 and the first film 11 (the first region 11a and the second region 11b) each include the third element (in the example, Cu).

Figure 4G:
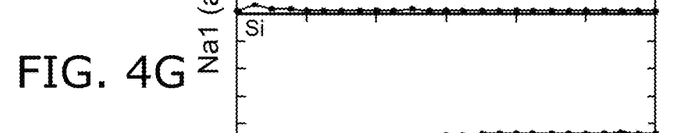

FIGS. 4C and 4G show the number of Si atoms. In the first layer 21, the second element (in the example, Si) is distributed in the depth direction from the front surface vicinity. On the other hand, in the first film 11, the second region 11b at the front surface vicinity does not include the second element. Or, the concentration of the second element in the second region 11b is less than the concentration of the second element in the first region 11a.

Figure 4H:
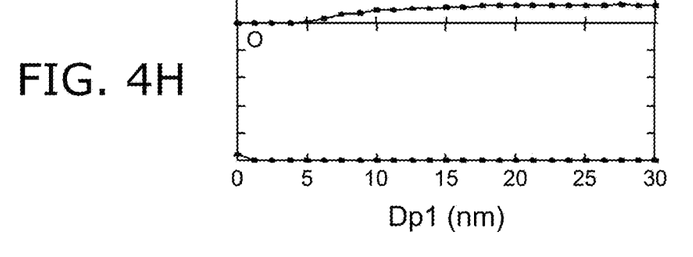

FIGS. 4D and 4H show the number of O atoms. In the first layer 21, O is distributed at the front surface vicinity. On the other hand, compared to the first layer 21, O is low at the front surface vicinity in the first film 11.

Thus, compared to the first layer 21, Si and O are reduced at the front surface vicinity (the second region 11b) in the first film 11. Compared to the interior (the first region 11a), Si is low at the front surface vicinity of the first film 11. Therefore, for example, a turf-like nanostructure that includes cavities is formed at the front surface vicinity. For example, the density of the second region 11b is less than the density of the first region 11a.

Hydrogen is drawing attention from the perspective of natural energy and clean energy. However, hydrogen is a combustible gas. To realize a hydrogen economy, a fast and low power-consumption hydrogen sensor for leakage detection is necessary.

Also, hydrogen occurs in various locations. It is desirable to detect phenomena by using hydrogen detection. For example, an initial fire can be detected by hydrogen detection because hydrogen is generated simultaneously with carbon monoxide in incomplete combustion. Healthcare can be assisted by predicting the intestinal environment by measuring the hydrogen gas in exhalation. Hydrogen is generated in such phenomena in ultra trace amounts. It is desirable to detect ultra trace amounts of hydrogen.

An oxide semiconductor-type sensor of a reference example is a hydrogen sensor that detects hydrogen. The hydrogen sensor of the reference example uses a heater to heat when detecting hydrogen. Therefore, the power consumption is large. Conversely, for example, a capacitance detection-type hydrogen sensor that uses a hydrogen-sensitive film including Pd can detect hydrogen without a heater. For example, the capacitance detection technique does not use a direct current. The power consumption can be reduced thereby.

A capacitive hydrogen sensor uses a hydrogen-sensitive film in which the volume changes due to absorbing/desorbing hydrogen. The capacitive hydrogen sensor uses a capacitance change to monitor the change of the strain of the hydrogen-sensitive film due to the absorbing/desorbing of hydrogen. Such a hydrogen-sensitive film can include a PdCuSi metallic glass. Thereby, for example, the hydrogen can quickly diffuse through the-sensitive film; and a fast response is possible. PdCuSi is a material that does not easily bond with hydrogen; therefore, the hysteresis when absorbing/desorbing hydrogen can be small. According to the embodiment, the first film 11 includes the first region 11a and the second region 11b described above. For example, the catalyst effect is stimulated thereby, and the detection of ultra trace amounts of hydrogen with a fast response is possible. The detection performance can be improved.

Second Embodiment

Figure 5:
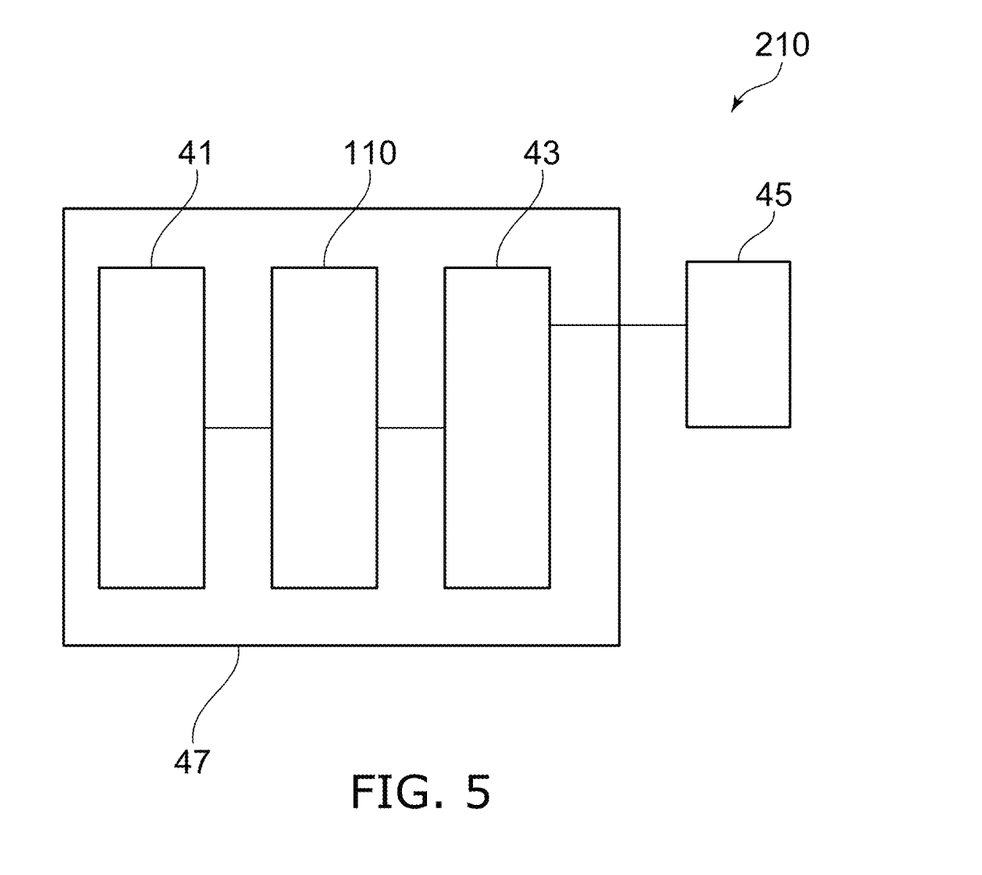
FIG. 5 is a block diagram illustrating a sensor according to a second embodiment.

FIG. 5 is a block diagram illustrating a sensor according to a second embodiment.

As shown in FIG. 5, the sensor 210 includes the sensor 110, a battery 41, a wireless communication circuit 43, an antenna 45, and a housing 47.

For example, the sensor 110, the battery 41, and the wireless communication circuit 43 are located inside the housing 47. At least a portion of the antenna 45 is located outside the housing 47. For example, the housing 47 is mounted to a ground surface, a floor, a wall, etc.

The battery 41 is connected to the sensor 110. The battery 41 is configured to supply electrical power to the sensor 110.

The wireless communication circuit 43 is connected to the sensor 110. The wireless communication circuit 43 is configured to transmit a signal corresponding to a value detected by the sensor 110.

The antenna 45 is connected with the wireless communication circuit 43. The signal is transmitted via the antenna 45.

Embodiments may include the following configurations (e.g., technological proposals).

Configuration 1

A sensor, comprising:
a sensor part including a first film including a first element,
the first element including at least one selected from the group consisting of Pd, Pt, and Au,
the first film including
a first region, and
a second region including a plurality of protrusions,
a protruding direction of the plurality of protrusions being along a first direction from the first region toward the second region.

Configuration 2

A sensor, comprising:
a sensor part including a first film including a first element,
the first element including at least one selected from the group consisting of Pd, Pt, and Au,
the first film including a first surface, a second surface, a first region, and a second region,
the first region being located between the first surface and the second surface,
the second region being located between the first region and the second surface,
the second surface being rougher than the first surface.

Configuration 3

The sensor according to Configuration 1 or 2, wherein
the first region is amorphous, and the second region includes a crystal grain, or
a crystallinity of the second region is greater than a crystallinity of the first region.

Configuration 4

The sensor according to Configuration 3, wherein
an average grain size of the crystal grains of the second region is not less than 0.1 nm and not more than 100 nm.

Configuration 5

The sensor according to any one of Configurations 1 to 4, wherein
the first region includes a second element including at least one selected from the group consisting of Si, P, and B, and
the second region does not include the second element, or a concentration of the second element in the second region is less than a concentration of the second element in the first region.

Configuration 6

The sensor according to any one of Configurations 1 to 5, wherein
the first region includes a third element including at least one selected from the group consisting of Cu, Ag, Ni, Au, Fe, and Cr.

Configuration 7

The sensor according to any one of Configurations 1 to 6, wherein
the second region includes oxygen, and
the first region does not include oxygen, or an oxygen concentration in the first region is less than an oxygen concentration in the second region.

Configuration 8

The sensor according to any one of Configurations 1 to 7, wherein
a concentration of the first element at a front surface of the first film is greater than a concentration of the first element at an inner portion of the first film.

Configuration 9

The sensor according to Configuration 1, wherein
a length in the first direction of the protrusion is not less than 0.1 nm and not more than 1000 nm.

Configuration 10

The sensor according to Configuration 1, wherein
a length of the protrusion in a second direction perpendicular to the first direction is not less than 0.1 nm and not more than 1000 nm.

Configuration 11

The sensor according to any one of Configurations 1 to 10, wherein
a thickness of the second region is not less than 1 nm and not more than 10 μm.

Configuration 12

The sensor according to any one of Configurations 1 to 11, wherein
a shape of the first film changes according to a concentration of a fourth element included in a gas around the sensor part.

Configuration 13

The sensor according to any one of Configurations 1 to 11, wherein
the sensor part includes a first electrode,
a gap is provided between the first film and the first electrode, and
a distance of the gap changes according to a concentration of a fourth element included in a gas around the sensor part.

Configuration 14

The sensor according to any one of Configurations 1 to 11, wherein
the sensor part includes:
a first electrode separated from the first film; and
a second electrode fixed to the first film, and
an electrostatic capacitance between the first electrode and the second electrode changes according to a concentration of a fourth element included in a gas around the sensor part.

Configuration 15

A manufacturing method, comprising:
preparing a first layer, the first layer including
a first element including at least one selected from the group consisting of Pd, Pt, and Au, and
a second element including at least one selected from the group consisting of Si, P, and B; and
forming a first film by ashing the first layer,
the first film including
a first region, and
a second region provided on the first region,
the second region including a plurality of protrusions,
a protruding direction of the plurality of protrusions being along a first direction from the first region toward the second region.

Configuration 16

The manufacturing method according to Configuration 15, wherein
the ashing includes:
first processing that uses a first gas; and
second processing that uses a second gas, and
an oxygen concentration of the first gas is greater than an oxygen concentration of the second gas.

Configuration 17

The manufacturing method according to Configuration 16, wherein
the second gas includes fluorine.

Configuration 18

The manufacturing method according to any one of Configurations 15 to 17, wherein
the second region includes oxygen, and
the first region does not include oxygen, or an oxygen concentration in the first region is less than an oxygen concentration in the second region.

Configuration 19

The manufacturing method according to any one of Configurations 15 to 18, wherein
the first region is amorphous, and the second region includes a crystal, or
a crystallinity of the second region is greater than a crystallinity of the first region.

Configuration 20

The manufacturing method according to any one of Configurations 15 to 19, wherein
the first region includes a second element, and
the second region does not include the second element, or a concentration of the second element in the second region is less than a concentration of the second element in the first region.

According to embodiments, a sensor and a method for manufacturing a sensor can be provided in which the detection performance can be improved.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as sensor parts, first films, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and methods for manufacturing sensors practicable by an appropriate design modification by one skilled in the art based on the sensors, and the methods for manufacturing sensors described above as embodiments of the invention also are within the scope of the invention to the extent that the purport of the invention is included.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a sensor part including a first film including a first element,
the first element including at least one selected from the group consisting of Pd, Pt, and Au,
the first film including
a first region, the first region including a first face and a second face, a direction from the first face toward the second face being along a first direction, and
a second region provided at the second face, the second region including a plurality of protrusions,
a protruding direction of the protrusions being along the first direction, and
the second region being not provided at the first face,
wherein the first region is amorphous, and the second region includes a plurality of crystal grains,
such that the detection performance of the sensor is improved.

2. The sensor according to claim 1, wherein
a crystallinity of the second region is greater than a crystallinity of the first region.

3. The sensor according to claim 2, wherein
an average grain size of the crystal grains of the second region is not less than 0.1 nm and not more than 100 nm.

4. The sensor according to claim 1, wherein
the first region includes a second element including at least one selected from the group consisting of Si, P, and B, and
the second region does not include the second element, or a concentration of the second element in the second region is less than a concentration of the second element in the first region.

5. The sensor according to claim 1, wherein
the first region includes a third element including at least one selected from the group consisting of Cu, Ag, Ni, Au, Fe, and Cr.

6. The sensor according to claim 1, wherein
the second region includes oxygen, and
the first region does not include oxygen, or an oxygen concentration in the first region is less than an oxygen concentration in the second region.

7. The sensor according to claim 1, wherein
a concentration of the first element at a front surface of the first film is greater than a concentration of the first element at an inner portion of the first film.

8. The sensor according to claim 1, wherein
a length in the first direction of the protrusion is not less than 0.1 nm and not more than 1000 nm.

9. The sensor according to claim 1, wherein
a length of the protrusion in a second direction perpendicular to the first direction is not less than 0.1 nm and not more than 1000 nm.

10. The sensor according to claim 1, wherein
a thickness of the second region is not less than 1 nm and not more than 10 μm.

11. The sensor according to claim 1, wherein
a shape of the first film changes according to a concentration of a fourth element included in a gas around the sensor part.

12. The sensor according to claim 1, wherein
the sensor part includes a first electrode,
a gap is provided between the first film and the first electrode, and
a distance of the gap changes according to a concentration of a fourth element included in a gas around the sensor part.

13. The sensor according to claim 1, wherein
the sensor part includes:
a first electrode separated from the first film; and
a second electrode fixed to the first film, and
an electrostatic capacitance between the first electrode and the second electrode changes according to a concentration of a fourth element included in a gas around the sensor part.

* * * * *